United States Patent [19]

Oren

[11] Patent Number: 5,649,533

[45] Date of Patent: Jul. 22, 1997

[54] THERAPEUTIC RESPIRATION DEVICE

[76] Inventor: Nathan Oren, Morad HaGai Street 56., Carmiel, Israel

[21] Appl. No.: 254,116

[22] Filed: Jun. 6, 1994

[30] Foreign Application Priority Data

Jun. 7, 1993 [IL] Israel ............................. 105930

[51] Int. Cl.$^6$ ............................. A62B 7/00
[52] U.S. Cl. .................. 128/207.12; 128/200.24; 128/206.21; 482/13
[58] Field of Search ............. 128/206.21, 200.24, 128/204.18, 204.26, 205.24, 205.25, 206.28, 207.12; 482/13

[56] References Cited

U.S. PATENT DOCUMENTS

| | | | |
|---|---|---|---|
| 3,710,780 | 1/1973 | Milch | 482/13 |
| 4,533,137 | 8/1985 | Sonne | 482/13 |
| 4,601,465 | 7/1986 | Roy | 482/13 |
| 4,739,987 | 4/1988 | Nicholson | 482/13 |

FOREIGN PATENT DOCUMENTS 565489  10/1993  France ...................... 482/13

*Primary Examiner*—V. Millin
*Assistant Examiner*—William J. Deane, Jr.
*Attorney, Agent, or Firm*—Ostrolenk, Faber, Gerb & Soffen, LLP

[57] ABSTRACT

A respiration device for preventing Sleep Apnea and snoring of patients. The device comprises a nose-mask and a housing with an inhalation and an exhalation, one-way, elastically self-closing, preferably diaphragm-type valves. The exhalation valve is adapted to close against a predetermined, elevated pressure prevailing in the housing prior to the completion of exhalation by the patient.

6 Claims, 3 Drawing Sheets

THERAPEUTIC RESPIRATION DEVICE

BACKGROUND OF THE INVENTION

The present invention relates to respiration aids, particularly for use by patients suffering from the disease known as Sleep Apnea and snoring. Sleep Apnea, which manifests itself by intensive snoring during sleep, is a biological disorder in the respiratory channels, in particular the upper air passages which tend to collapse and become blocked towards the end of every exhalation cycle. In order to overcome and avoid suffocation, the patient must exert an effort to continue the breathing process, i.e. the inhalation phase, which effort entails his actual awaking. Patients are thus driven into a serious mental and physical condition, due to accumulated lack of sleep; although the patients seem to be asleep, actually they are not deriving the benefits of slumber, not to mention the inconvenience caused to people in proximity.

In the course of medical research, it has been found that great relief is attained if, by some external means, the patient's lungs (and, of course, the upper bronchial passages included) be kept under a constant, slightly elevated air pressure, in the order of 5–15 CmH20 above the ambient, "atmospheric" pressure.

Experimental apparatus devised for the application of this kind of treatment included a vented nose-mask and snorkel, through which an excessive quantity of air was supplied to the patient (in the order of 100 lit/min while normal human air consumption during sleep is about 6 lit/min).

This method assured that both the inhalation and the exhalation took place under practically the same, elevated pressure, as required. However, it has been proved that the supply to the patient's mask of such extremely high quantities of air had caused him great inconvenience, expressed, inter alia, by extensive cooling and/or drying-up of his nose and other breathing passages.

It has been already proposed to overcome this inherent deficiency of the conventional systems—cf. Israel Patent Application No. 82300; however the apparatus therein disclosed still required the installation of an electric motor to drive the indispensable compressor.

It is therefore the prime object of the present invention to provide a respiration device for the purpose in question which is self-contained, i.e. without the provision of an electrically powered air compressor.

SUMMARY OF THE INVENTION

Thus provided according to the invention is a respiration device, particularly for preventing Sleep Apnea and snoring, comprising a housing defining an enclosed air chamber, a first opening in the housing, an inhalation, one-way, self-closing valve mounted to the first opening, a second opening in the housing, an exhalation, one-way, elastically self-closing valve mounted to the second opening, a third, breathing opening communicating with a nose-mask to be warn by a patient, said valves being operable to enable air flow into and from the chamber through said first and second openings, respectively, said exhalation valve being adapted to close against a predetermined, elevated pressure prevailing in the said chamber prior to the completion of exhalation by the patient.

The valve(s) are preferably of the type comprising an elastic, flap-type diaphragm.

BRIEF DESCRIPTION OF THE DRAWINGS

Further constructional details and advantages of the invention will be more fully understood in the light of the ensuing description of two preferred embodiments thereof, given by way of example only with reference to the accompanying drawings, wherein

FIG. 2b illustrates the exhalation phase of the device of FIG. 2a;

DETAILED DESCRIPTION OF THE PREFERRED EMBODIMENTS

Figure 1:
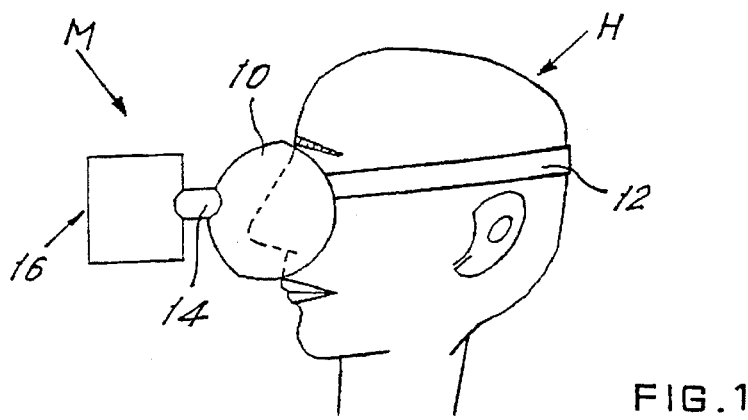
FIG. 1 is a schematic side elevation of a device according to a first embodiment of the invention.

In FIG. 1 there is shown a patient's head denoted H. The patient is wearing a respiration mask designating M comprising a nose cover 10 attached to the head by a rubber band 12. The cover 10 communicates through a tubular connector 14 to a valve controlled air-chamber housing generally denoted 16.

Figure 2A:
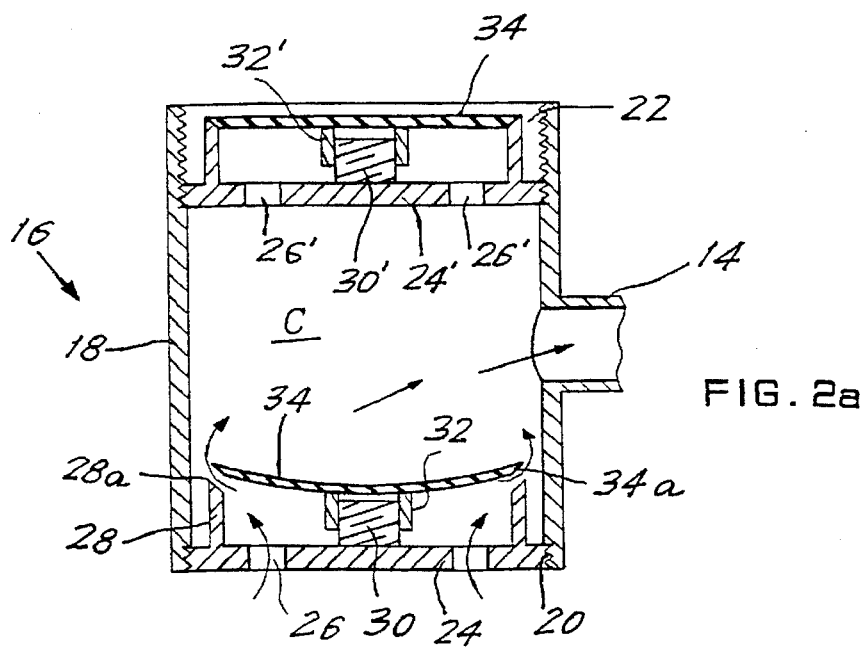
FIG. 2a is a cross-sectional view of the device of the FIG. 1, illustrating the inhalation phase.

Constructional details of the housing 16 are shown in FIG. 2a, namely: Tubular housing wall 18 is provided with lower and upper openings 20 and 22, both being internally screw-threaded as shown. An externally screw-threaded disc 24 is mounted to the opening 20, being formed with all-around deployed openings 26, only two of which being shown, and bearing therearound a projecting, cylindrical diaphragm valve seat portion 28, with faceted rim 28a.

At the center of the disc 24 a screw-threaded boss 30 is provided forming an attachment for bushing 32. The bushing 32 supports a circular rubber or the like elastic material diaphragm 34. The circumference 34a of the diaphragm is also facetted, complementary to facet 28a.

As will become clear later on, the diaphragm-based structure of the inhalation valve 34 is merely optional, and other types of self-closing, one-way valves can equally be used, such as common, hinged flap valves or the like.

In a similar manner, at the opening 22, disc 24' with series of openings 26', boss 30' and diaphragm 34' with support 32' are provided as shown. However, while the diaphragm 34 is of minimum flexibility e.g. designed to close on a pressure difference of, say 0.5 CmH20—the diaphragm is stiffer, designed to close against a pressure difference of the desired amount of 5–15 CmH20. Thus, a normally sealed air chamber C is formed within the housing 16.

An inhalation/exhalation cycle, as controlled by the diaphragm valves, will now be described with reference to FIGS. 2a and 2b, respectively.

During inhalation by the patient, a sub-pressure is generated within the chamber C by the lungs of the patient, which entrains the ingress of air around the diaphragm 34 (see arrows), the later being caused to withdraw and become bent inwards as shown in FIG. 2a.

Towards the end of the inhalation phase, i.e. when the sub-pressure which induces the entrance of air into the chamber C tends to equal the ambient pressure (less the said 0.5 CmH20), the elasticity of the diaphragm 34 (or equivalent) causes it to straighten and close against the valve seat portion 28. Therefore, for an intermediate period between the end of the inhalation and the start of the exhalation, both diaphragms 34 and 34' are closed.

Figure 2B:
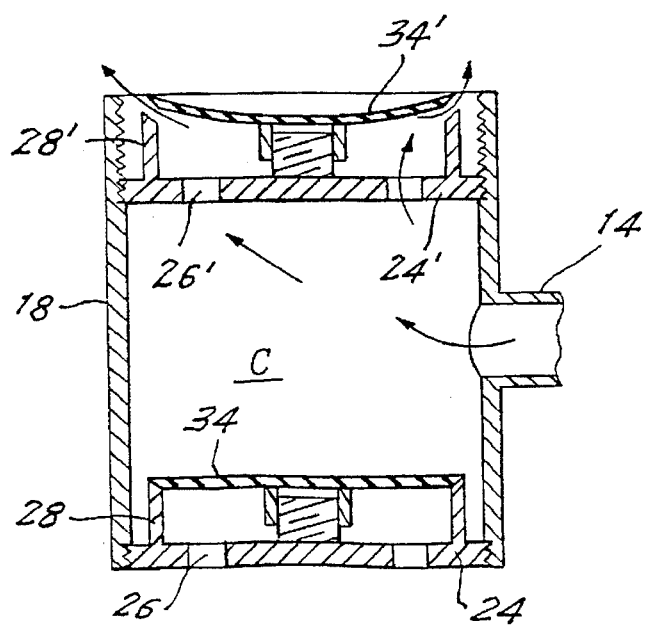

When the exhaustion phase begins, the roles of the diaphragms change in the sense that the elevated pressure generated by the patient lungs causes the diaphragm 34' to bend and allow the escape of air as illustrated by the arrows in FIG. 2b. Again, shortly before the termination of the exhalation cycle, the diaphragm 34' will resume its planar, sealing position. At this particular stage, the predetermined, elevated residual pressure becomes entrapped within the chamber C. This residual pressure is relayed to the patient, thus avoiding the phenomenon of air passage muscle collapse which is the very reason for the Sleep Apnea symptoms. As explained above, the amount of the residual pressure is governed by the elasticity of the diaphragm material and is preferably set to 5–15 CmH20.

Regarding the embodiment of FIGS. 3a and 3b, the main difference resides in that one of the residual pressure controlling valve is not a diaphragm based valve but is substituted by a spring loaded plunger arrangement as will be described further below. Complementary elements of construction will be denoted by similar numerals as in the preceding embodiment.

Hence, nose mask 110 is attached, e.g. by a screw-threaded nut 150 to an attachment member 152, attachable to a main housing member generally denoted 116. To one side wall of the housing 116 there is attached a sub-housing denoted 116' operated with a diaphragm based valve comprising diaphragm 134 and the remaining elements which are identical to the inhalation valve units of the embodiment of FIG. 2a.

The housing 116 is provided at one side thereof with a screw-threaded cap 154 including an adjustment spring tension screw 156. Screw 156 is connected by a weak coil spring 158 to a plunger 160, intermediate a press fitted disc 162 or any other equivalent arrangement. The plunger 160 is freely movable within cylinder housing 164 in a non-sealing manner, namely sliding on four or more ribs denoted 166 deployed inside the cylinder. The inner side of the plunger 160 is provided with a sharp lip 160a which seals an opening 170 when abutting against the flat surface 172 of the cylinder 164.

Figure 3A:
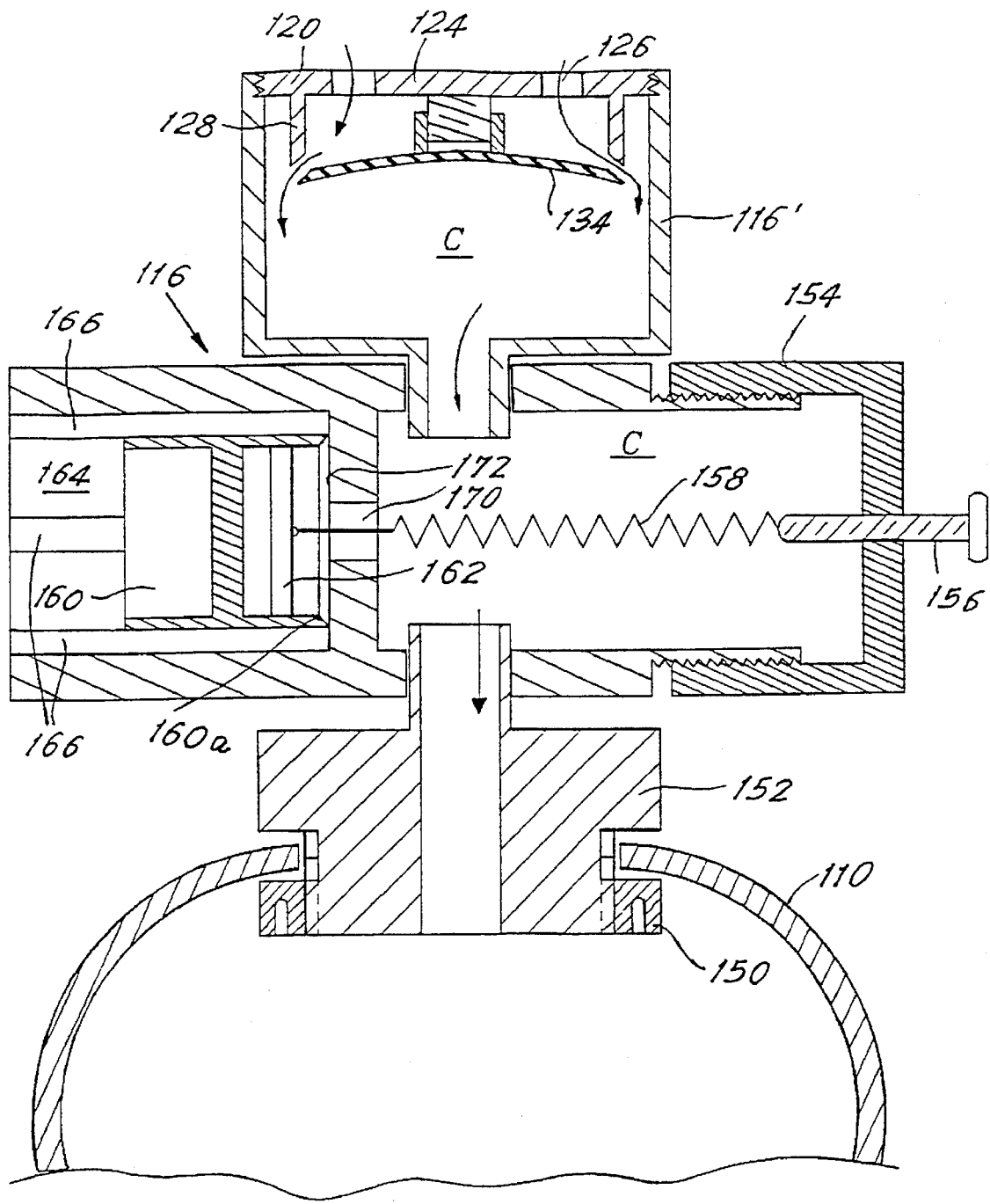
FIG. 3a shows another embodiment of the invention in the inhalation phase.
Figure 3B:
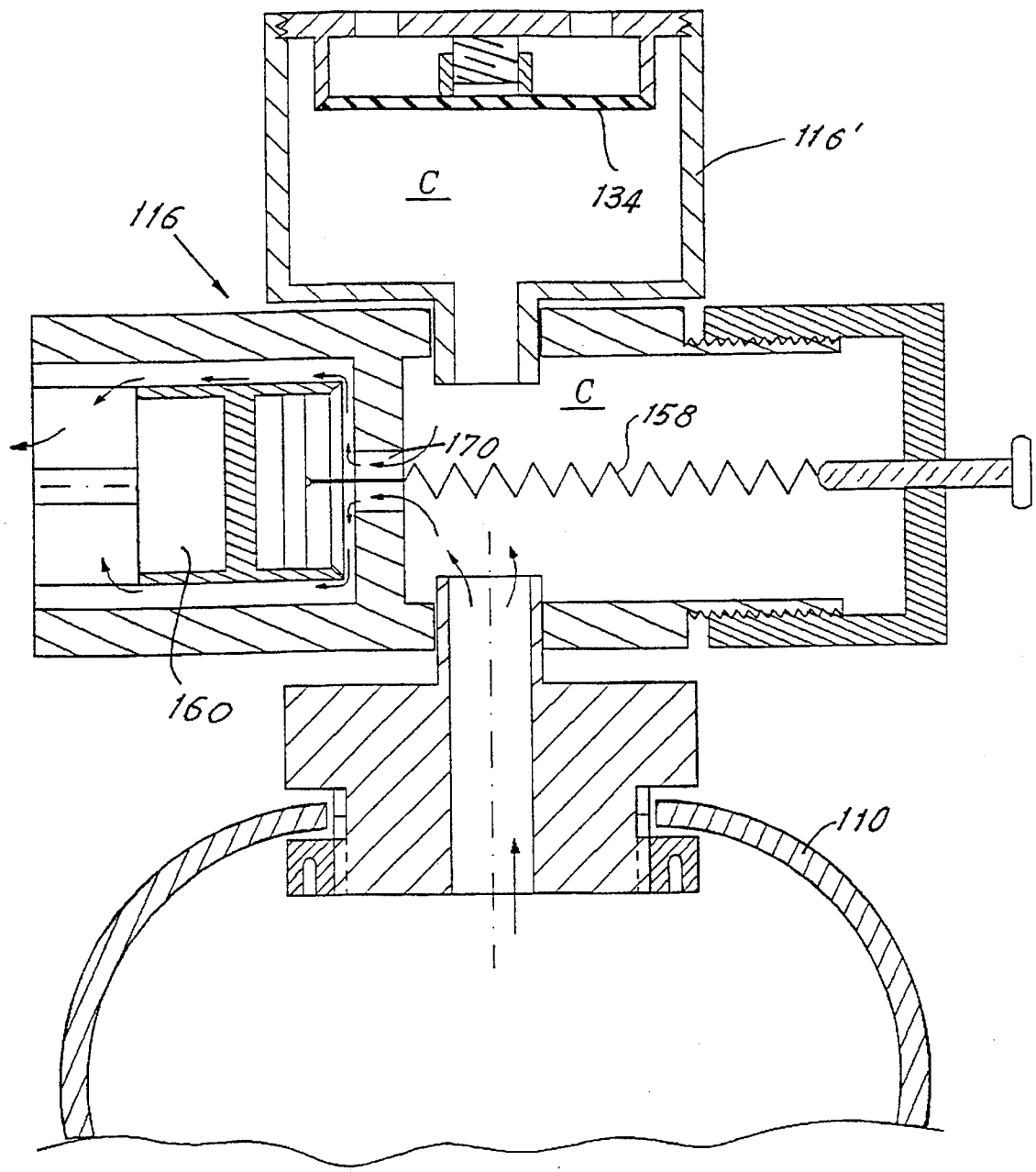
FIG. 3b shows the device of FIG. 3a in the exhalation phase.

It will therefore be readily understood that during the inhalation phase illustrated in FIG. 3a, air can enter the patient nose mask 110 through diaphragm valve 134. During the exhalation phase depicted in FIG. 3b, diaphragm 134 is closed and air can escape via opening 170 after the plunger 160 has been displaced to the left against the tension of the spring 158 by the exhalation pressure.

As in the previous embodiment, a residual, elevated pressure will be maintained inside the housing 116 (also 116') due to the interaction of the diaphragm 134 on the one hand and the displacement of the plunger 160 on the other hand, rendering the overall same effect.

It will be thus readily appreciated that the device provided according to the invention is most simple in construction; need not be associated with auxiliary installations such as electrical power source; it comprises a small number of elements and is therefore not liable to wear during prolonged use, and thus affordable by any suffering patient.

Those skilled in the art will readily appreciate that various changes, modifications and variations may be applied to the embodiments hereinbefore described without departing from the scope of the invention as defined in and by the appended claims.

What is claimed is:

1. A respiration device, particularly for preventing Sleep Apnea and snoring, comprising:

a housing defining an enclosed air chamber;

a first opening in the housing;

an inhalation, one-way, self-closing valve mounted to the first opening;

a second opening in the housing;

an exhalation, one-way, elastically self-closing valve mounted to the second opening;

a third, breathing opening communicating with a mask to be worn by a patient;

said valves being operable to enable air flow into and from the chamber through said first and second openings, respectively; and said exhalation valve being self-biased to close without additional assistance applied on the exhalation valve against a predetermined, elevated pressure higher than ambient pressure, prevailing in said chamber prior to the completion of exhalation by the patient.

2. The device as claimed in claim 1 wherein at least the said exhalation valve comprises an elastic, flap-type diaphragm.

3. The device as claimed in claim 2 wherein the diaphragm is circular, affixed at its center against one side of said housing.

4. The device as claimed in claim 3 wherein the diaphragm is sealable against a rim provided on a disc fastened to said opening(s).

5. The device as claimed in claim 1, where at least the said inhalation valve comprises an elastic, flat-type diaphragm.

6. The device as claimed in claim 2 where at least the said inhalation valve comprises an elastic, flat-type diaphragm.

* * * * *